United States Patent [19]

Richards

[11] 4,031,220
[45] June 21, 1977

[54] METHOD FOR THE TREATMENT OF MALARIA

[75] Inventor: William Henry George Richards, Orpington, England

[73] Assignee: Burroughs Wellcome Co., Research Triangle Park, N.C.

[22] Filed: Aug. 20, 1975

[21] Appl. No.: 606,004

[30] Foreign Application Priority Data

Aug. 20, 1974 United Kingdom ............ 36523/74

[52] U.S. Cl. ............................. 424/258; 424/263
[51] Int. Cl.$^2$ ................. A61K 31/47; A61K 31/44
[58] Field of Search ........................... 424/263, 258

[56] References Cited

UNITED STATES PATENTS 3,761,594  9/1973  Challey ............................. 424/258

OTHER PUBLICATIONS

Chemical Abst. vol. 66–75 8th Collective Index (1967–1971) p. 27121s.
Markley et al.–Chem. Abst. vol. 78 (1973) p. 23880m.
Ryley et al.–Annals of Trop. Med. & Parasit. vol. 64 No. 2 (1970) pp. 209–222.
Challey et al.–J. of Parasitology vol. 59 No. 3 (June 1973) pp. 502–504.

Primary Examiner—Sam Rosen
Attorney, Agent, or Firm—Donald Brown

[57] ABSTRACT

Pharmaceutical formulations and their preparation, suitable for use in the treatment or prophylaxis of malaria, which comprise a compound of formula (I)

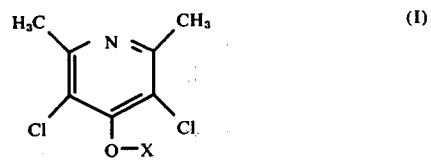

where X is hydrogen, an alkali metal, the ammonium radical, or H.(CH$_2$)$_n$.CO— where $n$ is 0 to 3, together with a compound of formula (II)

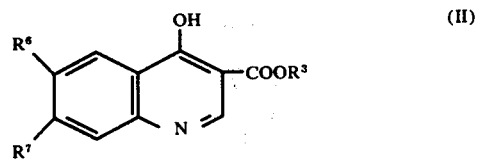

where R$^3$ is C1-C5 alkyl and R$^6$ and R$^7$ are the same or different and are each selected from alkyl, alkoxy, aralkoxy and di(C1-C5 alkyl)amino. Formulae (I) and (II) include pharmaceutically and pharmacologically acceptable acid addition salts of the respective compounds. Also provided is a method for the treatment of prophylaxis of malaria in a mammal comprising the administration to the mammal in combination of a compound of formula (I) and a compound of formula (II) as above defined.

9 Claims, No Drawings

METHOD FOR THE TREATMENT OF MALARIA

This invention relates to pharmaceutical formulations which have utility in the treatment or prophylaxis of malaria, and to a method for the treatment or prophylaxis of malaria in a mammal.

More particularly the present invention relates to pharmaceutical formulations which comprise a compound of formula (I)

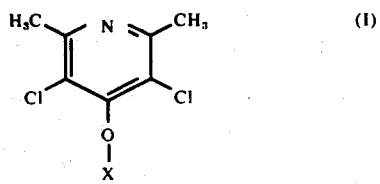

wherein X is hydrogen, an alkali metal, the ammonium radical ($NH_4-$), or a group $H(CH_2)_n \cdot CO-$ where $n$ is an integer from 0 to 3 together with a compound of formula (II)

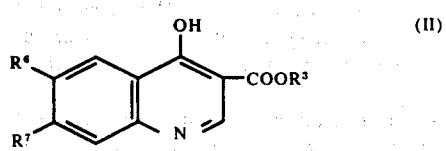

wherein $R^3$ is an alkyl group having 1 to 5 carbon atoms and $R^6$ and $R^7$ are the same or different and are each selected from alkyl, alkoxy, aralkoxy and di($C1$-$C5$ alkyl)amino wherein the alkyl groups are the same or different.

As examples of the groups $R^6$ and $R^7$ may particularly be mentioned
  alkyl having 2 to 18 carbon atoms;
  alkoxy having 2 to 18 carbon atoms; and
  (as examples of aralkoxy) phenethyloxy, phenylpropoxy,
  benzyloxy, p-chlorobenzyloxy, and p-aminobenzyloxy.

It will be appreciated that the compounds of formula (I) wherein X is hydrogen, together with those compounds of formula (II) wherein $R^6$ and/or $R^7$ is di($C1$-$C5$ alkyl) amino, form acid addition salts and formulae (I) and (II) should be understood to include pharmaceutically and pharmacologically acceptable acid addition salts of the respective compounds. Suitable salts that may be mentioned, by way of illustration, are the hydrochloride, hydrobromide and sulphate.

The compounds of formula (II) and certain of the compounds of formula (I) have separately been reported in the literature as having antimalarial activity, but it has now unexpectedly been found that the combination comprising a compound of formula (I) and a compound of formula (II) has a synergistic antimalarial effect. That is to say, the antimalarial effect of such a combination is greater than the sum of the separate antimalarial effects of each of the component compounds at the same dose levels. This synergism is illustrated in Table 1 which shows the activities, alone and in combination, of a compound of formula (I) (compound (A), X is hydrogen) and a compound of formula (II) (compound (B), $R^3$ is ethyl, $R^6$ is n-decyloxy, $R^7$ is ethoxy) against an experimental infection of *Plasmodium berghei* in mice.

The results were obtained in the following manner.

Heart blood from a mouse previously infected with a strain of *P. berghei* was introduced into a physiological solution (0.85% w/v sodium chloride and 1% w/v glucose) of glucose saline containing sufficient heparin to prevent blood clotting. The volume of this mixture was adjusted to prepare an inoculum in which there were one million infected red blood cells per 0.1 ml. Mice for test were then infected with 0.1 ml of the inoculum administered intraperitoneally. The mice were randomised, and then arranged in groups of five. One group was untreated controls, and each other group was given seven oral doses of a compound or combination, as appropriate, beginning on the afternoon of the day of infection, then twice a day for the following three days. On the fourth day blood smears were made from all the animals. These were stained and then examined. The parasitaemia of the mice treated with a compound or combination was estimated and recorded as a percentage of that of the untreated controls.

Table 1 shows that while there was a considerable (98% or more) reduction in parasitaemia when compounds (A) and (B) were used separately at dose levels only of 60 mg

TABLE 1

|  |  | Compound (A) mg base/kg ×7 oral | | | | | | | |
|---|---|---|---|---|---|---|---|---|---|
|  |  | 0 | 60 | 40 | 20 | 15 | 10 | 7.5 | 5 | 2.5 |
|  | 0 | 100 | 1.8* | 19.3 | 32.7 | 80* | 85.5 | NT | NT | NT |
|  | 4 | 0.2* | NT | NT | NT | NT | NT | NT | NT | NT |
| Compound (B) | 2 | 10.6 | NT | NT | NT | O* | NT | O* | NT | NT |
| mg base/kg | 1 | 57.5 | NT | NT | 0.1 | O* | 0.55 | 0.05* | 0.25 | 16.4 |
| ×oral | 0.5 | 72.5 | NT | NT | 0.1 | 0.02* | 1.65 | 0.53* | 45 | 45 |
|  | 0.25 | NT | NT | NT | 0.52 | 0.04* | 12.8 | 1.6* | 48.1 | 72 |

All results are the average of two experiments except (*), which are the results of a single experiment.
Compound (A): 3,5-dichloro-2,6-dimethyl-4-pyridinol.
Compound (B): ethyl 6-(n-decyloxy)-7-ethoxy-4-hydroxy-3-quinoline carboxylate.
NT: Not tested base/kg bodyweight and 4 mg base/kg bodyweight respectively, a comparable effect when the two were used in combination was obtained at levels of as little as 1/12 and 1/16 respectively of these individual doses when the other compound was present at a level of ½ of its individually effective dose or less. It will be appreciated however that the various compounds within formula (I) and formula (II) will differ quantitatively in their individual effect against a given malaria parasite and that the amounts of these compounds that are required in combination to effect a given reduction in parasitaemia will thus also vary.

While it is possible for the combination of a compound of formula (I) and a compound of formula (II) (hereinafter together referred to as the active ingredient) to be administered for the treatment or prophylaxis of malaria as the raw chemicals, it is preferable that the combination be presented as a pharmaceutical formulation. These formulations comprise an active ingredient (as above defined) together with one or more acceptable carriers therefor and optionally other therapeutic and/or prophylactic ingredients. The carrier(s) must be "acceptable" in the sense of being compatible with the other ingredients of the formulation and not deleterious to the recipient thereof.

The formulations include those suitable for oral rectal or parenteral (including intramuscular and intravenous) administration, although the oral is the preferred route. The formulations may, where appropriate, be conveniently presented in discrete dosage units and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active ingredient in a free-flowing form such as a powder or granules optionally mixed with a binder, lubricant, inert diluent, lubricating, surface active or dispersing agent. Moulded tablets may be made by moulding in a suitable machine a mixture of the powdered compound moistened with an inert liquid diluent. Tablets may be optionally coated and, if uncoated, may be optionally scored. Capsules may be prepared by filling the active ingredient, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Formulations suitable for oral administration wherein the carrier is a liquid may be presented as a solution or a suspension in an aqueous liquid or a non-aqueous liquid, or as an oil-in-water or water-in-oil liquid emulsion.

Formulations suitable for rectal administration wherein the carrier is a solid are most preferably presented as unit dose suppositories. Suitable carriers include cocoa butter and other materials commonly used in the art, and the suppositories may be conveniently formed by admixture of the active ingredient with the softened or melted carrier(s) followed by chilling and shaping in moulds.

Formulations suitable for parenteral administration include sterile solutions or suspensions of the active ingredient in aqueous or oleaginous vehicles. Such preparations are conveniently presented in unit dose or multidose containers which are sealed after introduction of the formulation until required for use.

It should be understood that in addition to the aforementioned carrier ingredients the formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

It will be appreciated that the amount required of an active ingredient for use in the treatment of prophylaxis of malaria will vary not only with the identities of the compound of formula (I) and the compound of formula (II), as has already been mentioned, but also with the route by which the active ingredient is administered. In general however a suitable dose for a mammal, including man, for the treatment of prophylaxis of malaria will lie in the range of 0.2 to 200 mg base per kilogram bodyweight of a compound of formula (I) and 0.005 to 15 mg base per kilogram bodyweight of a compound of formula (II).

A convenient unit dose formulation, for example a tablet, contains a compound of formula (I) in the range of 5.0 to 1000 mg (base) and a compound of formula (II) in the range of 0.125 to 75 mg. (base).

Methods for the preparation of the compounds of formulae (I) and (II) are well documented in the literature, for example in published U.K. Patent specifications Nos. 1,004,941 and 1,006,772 (formula (I)), and 1,168,801 and 1,219,721 (formula (II)).

It will be appreciated from the foregoing that what we will claim may comprise any novel feature described herein, principally and not exclusively, for example:

a. A pharmaceutical formulation suitable for use in the treatment of prophylaxis of malaria comprising a compound of formula (I) and a compound of formula (II), both as herein defined, together with a solid or liquid pharmaceutically acceptable carrier therefor, wherein when the carrier is a solid the formulation is presented as a unit dose formulation.

b. A method for the treatment of prophylaxis of malaria in a mammal comprising the administration to the mammal in combination of a compound of formula (I) and a compound of formula (II), both as herein defined.

c. A method for the preparation of a pharmaceutical formulation suitable for use in the treatment or prophylaxis of malaria comprising the admixture of a compound of formula (I) and a compound of formula (II), both as herein defined, together with a solid or liquid pharmaceutically acceptable carrier therefor and, when the carrier is solid, disposition into a unit dose formulation.

The following Examples are given purely by way of illustration of the present invention and should not be construed as in any way limiting the scope thereof.

Example 1

| Tablet formulation | |
|---|---:|
| Compound (A) (base) | 30. 0.mg |
| Compound (B) (base) | 0. 5.mg |
| Lactose | 60. 0.mg |
| Starch | 30. 0.mg |
| Polyvinylpyrrolidone | 10. 0.mg |
| Magnesium stearate | 2. 0.mg |

Compounds (A) and (B) were mixed together with the lactose and starch and the mixture then granulated with an aqueous solution of the polyvinylpyrrolidone. The magnesium stearate was added to the dried granules and the formulation compressed at 132.5 mg per tablet.

Compounds (A) and (B) are as identified in the foregoing Table 1.

Example 2

| Paediatric suspension formulation | | |
| --- | --- | --- |
| Compound (A) (base) | | 0.3 g |
| Compound (B) (base) | | 5.0 mg |
| Tragacanth | | 0.3 g |
| Acacia | | 0.3 g |
| Glycerin | | 10.0 g |
| Sucrose | | 50.0 g |
| Flavour | | q.s. |
| Methyl hydroxybenzoate | | 0.1 g |
| Purified water | to | 100.0 ml |

The tragacanth and acacia gums were dispersed in a solution of the methyl hydroxybenzoate in the glycerin, and to this was then added a solution of the sucrose in the bulk of the water. Compounds (A) and (B) were then slowly incorporated in the mixture to produce a smooth, homogeneous suspension which was diluted to volume with the remainder of the water after addition of the flavour.

Each 5 ml dose contained:

| Compound (A) | 15.00 mg |
| --- | --- |
| Compound (B) | 0.25 mg |

Compounds (A) and (B) are as identified in the foregoing Table 1.

EXAMPLE 3

In vivo demonstration of synergistic antimalarial effect

The antimalarial effect of combinations of compound (A) as identified hereinabove (Table 1) with compounds of formula (II) was determined against an experimental infection of *Plasmodium berghei* in mice, in the same manner as described hereinabove in respect of the combination of compounds (A) and (B). For each combination the antimalarial effect was found to be greater than the sum of the separate antimalarial effects of each of the component compounds at the same dose levels.

Combination (i)

Compound (A) plus ethyl 7-diethylamino-4-hydroxy-6-n-propylquinoline-3-carboxylate.

Combination (ii)

Compound (A) plus ethyl 4-hydroxy-7-isobutyl-6-n-propoxyquinoline-3-carboxylate.

What we claim is:

1. A method for the treatment or prophylaxis of malaria in a mammal which might be exposed to malaria or suffering from malaria which comprises the administration to the mammal of a non-toxic, effective antimalarial treatment or prophylaxis amount of the formulation comprising:

(a) a compound of the formula (I)

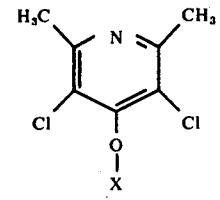

wherein X is hydrogen, an alkali metal, the ammonium radical or a group $H(CH_2)_n.CO-$ where $n$ is an integer from 0 to 3, or a pharmaceutically and pharmacologically acceptable acid addition salt thereof when X is hydrogen; and b. a compound of formula II

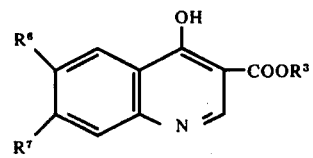

wherein $R^6$ is n-decyloxy, $R^7$ is ethoxy and $R^3$ is ethyl or a pharmaceutically and pharmacologically acceptable acid addition salt thereof.

2. A method according to claim 1 wherein the compounds are administered by the oral route.

3. A method according to claim 1 which comprises administration of the compound of formula (I) at a dose in the range of 0.2 to 200 mg. (calculated as the base) per kilogram mammal body weight and administration of the compound of formula (II) at a dose in the range 0.005 to 15 mg. (calculated as the base) per kilogram mammal body weight.

4. A method according to claim 1 wherein the mammal is man.

5. The method of claim 1 wherein the compound of formula (II) is ethyl 6-n-decyloxy-7-ethoxy-4-hydroxy-3-quinoline carboxylate.

6. The method of claim 1 wherein the compound of formula (I) is 3,5-dichloro-2,6-dimethyl-4-pyridinol or a pharmaceutically and pharmacologically acceptable acid addition salt thereof.

7. The method of claim 5 wherein the compound of formula (I) is 3,5-dichloro-2,6-dimethyl-4-pyridinol or a pharmaceutically and pharmacologically acceptable acid addition salt thereof.

8. The method of claim 7 in which the mammal is man.

9. The method of claim 8 in which the formulation is administered orally.

* * * * *